United States Patent [19]

Hundeck et al.

[11] Patent Number: 4,672,142
[45] Date of Patent: Jun. 9, 1987

[54] PROCESS FOR MAKING 1,2-DICHLOROETHANE

[75] Inventors: Joachim Hundeck, Bonn; Harald Scholz, Erftstadt; Hans Hennen, Hürth; Bernhard Kuxdorf, Brühl; Herbert Püsche, Erftstadt, all of Fed. Rep. of Germany

[73] Assignee: Hoechst Aktiengesellschaft, Fed. Rep. of Germany

[21] Appl. No.: 419,084

[22] Filed: Sep. 16, 1982

[30] Foreign Application Priority Data

Sep. 21, 1981 [DE] Fed. Rep. of Germany ....... 3137513

[51] Int. Cl.$^4$ .............................................. C07C 17/02
[52] U.S. Cl. .................................... 570/247; 570/253; 570/254
[58] Field of Search ............... 570/252, 253, 247, 242, 570/262, 246, 254

[56] References Cited

U.S. PATENT DOCUMENTS

| | | | |
|---|---|---|---|
| 3,839,475 | 10/1974 | Kurtz et al. ......................... | 570/247 |
| 3,985,816 | 10/1976 | Tsao .................................... | 570/246 |
| 4,347,391 | 8/1982 | Campbell ............................ | 570/252 |

FOREIGN PATENT DOCUMENTS

| | | | |
|---|---|---|---|
| 6404193 | 8/1965 | Netherlands ........................ | 570/246 |
| 1022253 | 3/1966 | United Kingdom ................ | 570/246 |

Primary Examiner—Michael L. Shippen
Assistant Examiner—Joseph A. Boska
Attorney, Agent, or Firm—Connolly and Hutz

[57] ABSTRACT

The disclosure relates to a process for making 1,2-dichloroethane by reacting ethylene and chlorine in a reaction zone having a liquid medium containing chlorinated $C_2$-hydrocarbons circulated therein. To this end, the disclosure provides:

(a) for approximately equimolar proportions of ethylene and chlorine to be introduced into the circulated liquid medium; for the whole to be reacted in a reaction zone at a temperature of about 75° up to 200° C. under a pressure of about 1 up to 15 bars, the mean sojourn time of the reaction mixture in the mixing zone and reaction zone being equal to about 1 to 15 hours;

(b) for a portion of liquid reaction mixture to be removed from the reaction zone and subdivided into two streams, for one of these streams to be passed through a heat exchanger for the abstraction of calorific energy and reduction of its initial temperature, and for it to be recycled to the mixing and reaction zone; for the second stream to be introduced into an expansion vessel and for proportions corresponding to the quantity of reaction product formed in the reaction zone to be evaporated therein; for resulting vaporous matter to be introduced into a fractionating column, unevaporated liquid matter of the second stream being recycled into the liquid medium circulated in the mixing and reaction zone; and (c) for 1,2-dichloroethane to be distillatively separated from the vaporous matter introduced into the fractionating column with the use of a portion of the heat energy transferred inside the heat exchanger and for the 1,2-dichloroethane to be removed overhead.

10 Claims, 1 Drawing Figure

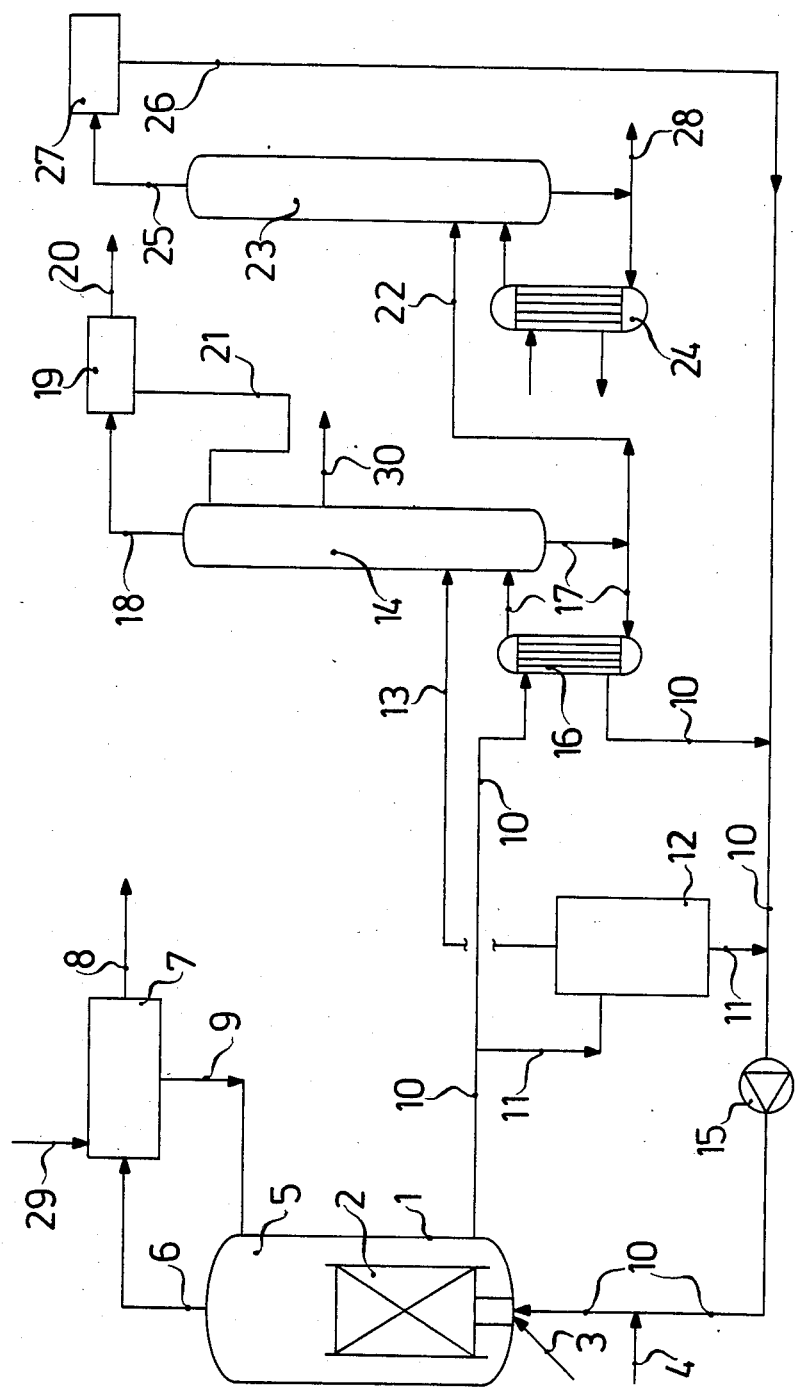

PROCESS FOR MAKING 1,2-DICHLOROETHANE

The present invention relates to a process for making 1,2-dichloroethane by reacting ethylene and chlorine in liquid 1,2-dichloroethane in the presence of a customary catalyst, technically beneficial use being made of the reaction heat which is evolved during the reaction and the undesirable formation of higher chlorinated products, such as tri-, tetra- and pentachloroethane, inside the reactor being extensively avoided as well as the accumulation of such products therein.

The chlorination of olefins by means of chlorine is known to take place in an exothermal reaction. In the event of ethylene being chlorinated with chlorine, 2200 kJ heat is evolved per kg 1,2-dichloroethane. This means in other words that a quantity of heat sufficient for the generation of about 1 ton steam is evolved upon the production of 1 ton 1,2-dichloroethane. In the processes for making 1,2-dichloroethane described heretofore, the reaction heat has either been abstracted by cooling the reactor or used partially for directly evaporating and expelling the dichloroethane formed during the reaction from the reaction mixture or reactor, and in some case or other partially or completely but exclusively for rectifying 1,2-dichloroethane originating from a third source.

The process described in DE-PS No. 15 43 108, for example, provides for the combined abstraction of the reaction heat which is evolved during the chlorination of ethylene with chlorine. More especially, the iron reactor used for carrying out the reaction is provided with a cooling means which is supplied with cooling water permitting the heat evolved during the reaction to be abstracted and a predetermined reaction temperature of 50° up to 70° C. to be maintained. The reaction temperature is lower than the boiling point of 1,2-dichloroethane and is controlled during the reaction so as to ensure continuous removal of the 1,2-dichloroethane formed in vapor form from the reaction chamber. While no higher chlorinated products accumulate in this process inside the reactor, the fact remains that 3.3% trichloroethane is being formed and that the reaction heat remains unutilized as it is necessary for condensed 1,2-dichloroethane to be freed from the by-product just specified.

A process basically the same as that described in DE-PS No. 15 43 108 has been disclosed in DE-OS No. 29 35 884, this latter process comprising: during the reaction, circulating the material placed in the reactor through an annular conduit communicating with the reactor and separating gaseous products issuing at the head of the reactor in a rectifying column with recovery of 1,2-dichloroethane. Higher boiling by-products are recycled from the base portion of the rectifying column to the reactor; this however is disadvantageous as reaction base product which is removed discontinuously is required to be worked up separately, and as the reaction heat evolved is utilized partially only.

A further process for making ethylene chloride (cf. DE-OS No. 24 27 045) provides:

(a) for ethylene and chlorine to be introduced into a reaction zone maintained under elevated pressure and having a liquid medium containing chlorinated $C_2$-hydrocarbons or mixtures thereof circulated therein, the medium being kept at a temperature lower than its evaporation temperature under the pressure prevailing inside the reaction zone with formation of crude liquid ethylene dichloride;

(b) for the crude liquid ethylene dichloride to be introduced together with the circulated medium into a zone maintained under lower pressure than the reaction zone, the said zone being maintained under a pressure and at a temperature at which the crude ethylene dichloride becomes evaporated under the action of the reaction heat set free during the reaction of chlorine with ethylene, and (c) for vaporous crude ethylene dichloride to be introduced into a rectifying zone and to be rectified therein with the aid of the reaction heat set free during the reaction of chlorine with ethylene, purified ethylene dichloride being removed from the rectifying zone, and product obtained in the base portion of the rectifying column being recycled to the above zone maintained under lower pressure, and combined with the medium circulated therein.

Recycling the base product into the reactor is disadvantageous inasmuch as the circulated liquid medium becomes enriched with higher boiling chlorination products which must successively be removed therefrom. As indicated in Example 4 of DE-OS No. 24 27 045 the circulated medium contains an about 60% proportion of 1,1,2-trichloroethane. This means in other words that the chlorination reaction described heretofore is accompanied by the formation of considerable proportions of undesirable by-products.

It has therefore been desirable to improve the processes described heretofore so as to extensively avoid the formation of by-products and provide for an optimum utilization of the reaction heat which is evolved. To this end, it is primarily necessary for the quantity of crude dichloroethane produced per unit time to be continuously removed in vapor form from the reaction mixture after a predetermined reaction period of the reactants, and for it to be purified in a separate rectifying column. Higher chlorinated by-products which may optionally be produced as base-products are taken from the rectifying column and utilized without being recycled to the reaction zone receiving the feed materials. The crude dichloroethane can be rectified with the aid of the calorific energy set free upon the reaction of ethylene with chlorine, the calorific energy balance portion which is not needed for the rectification being used outside the present process, e.g. for the generation of steam.

The present invention relates more particularly to a process for making 1,2-dichloroethane by reacting ethylene and chlorine in a reaction zone having a liquid medium containing chlorinated $C_2$-hydrocarbons circulated therein at a temperature lower than the evaporation temperature of said medium under the pressure prevailing inside the reaction zone, in the presence of a customary chlorination-inducing catalyst and optionally an inhibitor reducing the formation of by-products so as to obtain crude 1,2-dichloroethane, removing the crude dichloroethane from the reaction zone and purifying it in a separate downstream fractionating zone, which comprises:

(a) introducing approximately equimolar proprotions of ethylene and chlorine into the circulated liquid medium; intensively mixing the whole in a mixing zone and then reacting the mixture in a reaction zone at a temperature of about 75° up to 200° C. under a pressure of about 1 up to 15 bars, the mean sojourn time of the reaction mixture in the mixing zone and reaction zone being equal to about 1 to 15 hours;

(b) removing a portion of the liquid reaction mixture from the reaction zone and subdividing said portion into two partial streams, passing one of these partial streams through a heat exchanger for abstraction of calorific energy and reduction of its initial temperature and recycling it to the mixing and reaction zone; introducing the second partial stream into an expansion vessel and evaporating therein a proprotion corresponding to the quantity of reaction product formed in the reaction zone and optionally also a proportion of 1,2-dichloroethane originating from a third source and being introduced into the reaction zone; introducing resulting vaporous matter into a fractionating column and recycling unevaporated liquid matter of the second partial stream into the liquid medium circulated in the mixing and reaction zone; and (c) separating distillatively 1,2-dichloroethane from the vaporous matter introduced into the fractionating column with the use of a portion of the heat energy transferred inside the heat exchanger and removing the 1,2dichloroethane overhead, higher chlorinated products being obtained in the column's base portion from which they are removed and worked up separately.

A preferred feature of the present process provides for the reaction of ethylene with chlorine to be effected at a temperature of 95° up to 160° C., preferably under a pressure of 1 up to 15 bars and over a mean period of time of 2 up to 10 hours. The circulated liquid medium should preferably and predominantly consist of 1,2-dichloroethane which may be slightly contaminated with higher ethylene chlorination products formed as by-products during the reaction. The partial stream of reaction mixture removed for effecting heat exchange is passed through the heat exchanger and then recycled with a temperature which is by about 5° up to 50° C. lower than its initial temperature into the mixing and reaction zone.

In the event of the feed materials being diluted with inert gases, it is good practice for the latter to be taken from the reaction mixture together with the low-boiling chlorinated hydrocarbons, such as ethyl chloride, by removing them from the upper portion of the reaction zone, cooling them in a condenser placed downstream thereof, dichloroethane which issues together with the inert gas being condensed and recycled into the reaction zone, or being used otherwise.

The process of this invention can finally be used for purifying crude 1,2-dichloroethane made by a process other than described in the present invention. To this end crude dichloroethane is either introduced into the condenser placed downstream of the reactor and delivered via the condenser outlet to the reaction zone, or it is introduced into one of the two partial streams of material specified, after heat exchange or evaporation, but prior to their being recycled to the reaction zone. The quantity of circulated reaction mixture which is taken from the reaction zone, is equal to about 3 up to 30 times the reactor volume. Heat which is evolved can be utilized for rectifying the 1,2-dichloroethane produced and of an additional quantity of separately produced 1,2-dichloroethane, or outside the present process for heating purposes or for the generation of steam.

The following statements are intended further to illustrate the process of this invention.

It is possible for the chlorine and ethylene reactants to be diluted with inert gases. The chlorine can be introduced inbto the mixing zone in the form of liquid or gaseous matter, liquid chlorine being preferably evaporated ahead of the reactor in a heat exchanger with the aid of a portion of the reaction enthalpy. Iron-III chloride should preferably be used as a catalyst and oxygen should preferably be used as an agent inhibiting the formation of by-products.

With respect to the liquid medium in the reactor, it is possible for it to be circulated by means of a pump and/or in accordance with the principle underlying a thermosiphon or mammouth pump. Inside the mixing zone, the liquid medium should conventiently be circulated with a velocity of at least 0.1 m/second. The circulation for heat exchange and evaporation can also be effected with the aid of a pump and/or in accordance with the principle underlying a thermosiphon; it is even possible for these two operations to be effected successively with the use of just one liquid medium cycle.

An exemplary manner of carrying out the process of this invention will now be described with reference to the accompanying drawing. Needless to say the invention is not limited to the embodiment described.

Liquid 1,2-dichloroethane is introduced into a cylindrical reactor 1 which has a cylindrical structure 2 open at its lower and upper ends placed therein, the cylindrical structure 2 being filled with packing material or having accessory equipment provided therein. Next, ethylene is introduced into reactor 1 through line 3 and chlorine gas is introduced through line 4 to effect circulation of the 1,2-dichloroethane in accordance with the principle underlying a mammouth pump. Once the ethylene has commenced reacting with the chlorine gas, the reaction being started inside the mixing zone and completed inside reaction zone 5, additional buoyant forces occur inside the inner cylindrical structure 2 which result from inert gases contained in the feed materials and from the temperature difference caused by reaction heat set free. The temperature prevailing inside reactor 1 is slightly lower than the boiling temperature of 1,2-dichloroethane inside the reactor under the pressure prevailing. Inert gases which may be found to be present in reactor 1 are removed through line 6 and cooled in cooler 7 in order to condensate vaporous 1,2-dichloroethane which may have been carried along. Uncondensed gas is allowed to escape through line 8 whilst the condensate is recycled into reactor 1 through line 9. By regulating the flow of inert gas, it is possible to establish the pressure desired to prevail in reactor 1. Line 29 is used for the supply of crude 1,2-dichlorethane from a third source.

To remove produced 1,2-dichloroethane from reactor 1, a stream of liquid reaction mixture is taken from the reactor through line 10, and subdivided into two partial streams; one of these two partial streams delivers its heat content to heat exchanger 16; it is recycled through cycle line 10 into reactor 1 whilst the other is introduced through line 11 into expansion vessel 12. The quantity of liquid matter taken from reactor 1 is equal to about 15 times the total volume of the material in the reactor.

In expansion vessel 12, the stream of liquid matter introduced thereinto is treated so as to evaporate a quantity adequate to the reaction product formed in the reaction zone, the resulting vaporous matter being introduced through line 13 into fractionating column 14, whilst unevaporated liquid matter is taken from expansion vessel 12 and recycled through lines 11 and 10 and by means of pump 15 into reactor 1. The vaporous matter introduced into column 14 is fractionately distilled therein. The heat energy needed for this is taken from heat exchanger 16 by the introduction of product accumulating in the base of column 14 through cycle line 17 into heat exchanger 16. Pure 1,2-dichloroethane is removed at the head of column 14 through line 18, condensed in cooler 19 and taken therefrom through line 20. A portion of the condensate is used as reflux in column 14 and introduced thereinto through line 21. In the event of the mixture which is distilled in column 14 containing 1,2-dichloroethane and lower boiling components, these latter are removed through line 20 and 1,2-dichloroethane is removed through line 30.

To intensify the decontamination of the product obtained in the base portion of column 14, which essentially consits of higher chlorinated products of ethylene and minor residual proportions of 1,2-dichloroethane, it is possible for it to be introduced through lines 17 and 22 into column 23, and to be distilled therein, under vacuum. The heat energy necessary for effecting the distillation can again be taken from a heat exchanger 24, whose heat requirements can be met by the reaction enthalpy. The head product of column 23 is liquefied in condenser 27 and then recycled through lines 25, 26 and 10 into reactor 1, the base product of column 23 being removed through line 28.

The process of this invention compares favorably with the prior art methods in various aspects. One technically beneficial effect results from the continuous removal of a portion of liquid matter from the reactor and its division into two partial streams of which one permits reaction heat to be continuously recovered and transferred, and the other is partially evaporated, of which only the evaporated portion is worked up; as a result, it is ensured that catalyst-free crude dichloroethane is introduced into the fractionating column, which also receives the higher chlorinated by-products together with the evaporated matter. In other words, the liquid matter portion of the second partial stream, reduced by the by-products formed during the reaction, is recycled into the reactor so that by-products are substantially not liable to accumulate in the reactor base portion. In the processes described heretofore, these by-products have been found to give rise to the concentration of higher chlorinated by-products which ultimately must invariably be removed from the reactor base portion. Needless to say catalyst losses are associated therewith which naturally affect the commerical attractiveness of these processes. Under the reaction conditions used in accordance with this invention, the mean sojourn time of all reactants inside the reactor is shortened so that undesirable side-reactions involving by-product formation are extensively avoided. Last not least, the present process permits use to be made of feed materials contaminated with inert gases which are known to entail difficulties in the decontamination of dichloroethane in the fractionating column. In accordance with this invention, the inert gases are already removed from the reactor via an inert gas removal line so that they are definitely prevented from affecting the work-up of the reaction mixture. No special expensive device need be used for carrying out the present process. It is possible to use slightly modified standard utilities such as those customarily employed for an addition chlorination of ethylene. Needless to say this adds further to the commercial attractiveness of the present process.

EXAMPLE

Reactor 1, which had a volume of about 25 m$^3$, was initially fed with 20,000 liter 1,2-dichloroethane which was then admixed with 300 mg iron-III chloride per kg 1,2-dichloroethane as a catalyst. 2277 kg ethylene, 5737 kg chlorine gas containing about 4 volume % inert gases, and 20 m$^3$ (S.T.P.) air were introduced into the reactor under a pressure of 2.5 bars and at a temperature of 105°–110° C.

In order to remove the 1,2-dichloroethane produced in reactor 1 and reaction heat, a stream of liquid reaction mixture was taken from reactor 1 through cycle line 10, subdivided into two partial streams, of which one delivered its heat content to heat exchanger 16; it was recycled through cycle line 10 into reactor 1. The other partial stream was introduced through line 11 into expansion vessel 12. About 350 m$^3$/h reaction mixture was circulated through the heat exchanger cycle, whilst about 8000 kg crude 1,2-dichloroethane was evaporated from the partial stream cycled through the expansion vessel 12.

The 1,2-dichloroethane introduced through line 13 into distilling column 14 contained about 0.1 wgt % 1,1,2-trichloroethane and about 0.01 wgt % ethyl chloride and 1,1-dichloroethane. High-boiling components originating from the reaction mixture inside reactor 1 could not be found to have concentrated inasmuch as the by-products formed during the low 3 to 4-hour reaction time were completely removed together with vaporous dichlorethane from expansion vessel 12. The base temperature in distilling column 14 was about 78° C.

The off-gas coming from the reactor 1 was introduced through line 6 into cooler 7. 102 m$^3$/h uncondensed matter of the off-gas containing 2.5 volume % 1,2-dichloroethane and 3 volume % each of ethyl chloride and ethylene was removed through line 8 and delivered to an incinerator.

Low boiling matter was removed from distilling column 14 through line 20. The base product of column 14 was introduced through lines 17 and 22 into column 23 and 1,1,2-trichloroethane was separated therein. 7972 kg/h 1,2-dichloroethane was removed from column 14 through lateral outlet 30.

We claim:

1. In the process for making 1,2-dichloroethane by reacting ethylene and chlorine in a reaction zone having a liquid medium containing chlorinated C$_2$-hydrocarbons circulated therein at a temperature lower than the evaporation temperature of said medium under the pressure prevailing inside the reaction zone, in the presence of a conventional chlorination-inducing catalyst so as to obtain crude 1,2-dichloroethane, removing the crude dichloroethane from the reaction zone and purifying it in a separate downstream fractionating zone, the improvement which comprises:

(a) introducing approximately equimolar proportions of ethylene and chlorine into the circulated liquid medium; intensively mixing the whole in a mixing zone and then reacting the mixture in a reaction zone at a temperature of about 75° up to 200° C. under a pressure of about 1 up to 15 bars, the mean sojourn time of the reaction mixture in the mixing zone and reaction zone being equal to about 1 to 15 hours;

(b) removing a portion of the liquid reaction mixture from the reaction zone and subdividing said portion into two partial streams, passing one of these partial streams through a heat exchanger for extraction of chlorific energy and reduction of its initial temperature and recycling it to the mixing and reaction zone; introducing the second partial stream into an expansion vessel and evaporating therein a proportion corresponding to the quantity of reaction product formed in the reaction zone; introducing resulting vaporous mater into a fractionating column and recycling unevaportated liquid matter of the second partial stream into the liquid medium circulated in the mixing and reaction zone; and (c) separating distillatively 1,2-dichloroethane from the vaporous matter introduced into the fractionafing column with the use of a portion of the heat energy transferred inside the heat exchanger and removing the 1,2-dichloroethane overhead, higher chlorinated products being obtained in the column's base portion from which they are removed and worked up separately.

2. The process as claimed in claim 1, wherein the liquid medium circulated consists essentially of 1,2-dichloroethane.

3. The process as claimed in claim 1 or 2, wherein the ethylene and chlorine are reacted at a temperature of 95° to 160° C., under a pressure of 1 to 15 bars over a mean period of 2 to 10 hours.

4. The process as claimed in claim 1, wherein one of the two partial streams of the liquid reaction mixture is passed through the heat exchanger and recycled to the mixing and reaction zone with a temperature 5° to 50° C. lower than its initial temperature.

5. The process as claimed in claim 1, wherein inert gases or low-boiling chlorinated hydrocarbons, such as ethyl chloride, being contained in the reaction mixture are removed from the upper portion of the reaction zone, cooled in a condenser mounted downstream thereof so as to effect condensation of dichloroethane which escapes together with the issuing gas, the condensed dichloroethane being recycled to the reaction zone or used otherwise.

6. The process as claimed in claim 1, wherein 1,2-dichloroethane orginating from a third source is either introduced in to the downstream condenser or recycled through the condenser outlet into the reaction zone, or introduced ahead of the reaction zone into one of the two partial streams aforesaid, prior to subjecting the partial stream to heat exchange or prior to effecting the evaporation of a portion thereof.

7. The process as claimed in claim 1, wherein a quantity of circulated reaction mixture approximately equal to 3 up to 30 times the reactor volume is taken from the reaction zone.

8. The process as claimed in claim 1, wherein resulting utilizable calorific energy is used for rectifying the 1,2-dichloroethane produced and an additional quantity of the 1,2-dichloroethane originating from the third source.

9. The process as claimed in claim 1, wherein resulting utilizable calorific energy is wholly or partially utilized outside the process for heating purposes or for the generation of steam.

10. The process as claimed in claim 1, wherein substantially none fo the higher chlorinated products obtained in said step (c) remain with the unevaporated matter recycled according to said step (b).

* * * * *